United States Patent [19]

Cherlo

[11] Patent Number: 4,956,589
[45] Date of Patent: Sep. 11, 1990

[54] INTEGRATED TOOL CONTROL FOR WORK STATION

[76] Inventor: Victor M. Cherlo, 127 Archer Ave., Mount Vernon, N.Y. 10550

[21] Appl. No.: 283,121

[22] Filed: Dec. 12, 1988

[51] Int. Cl.$^5$ ............................................. H02P 7/36
[52] U.S. Cl. ........................................ 318/67; 318/59
[58] Field of Search .................. 318/51, 53, 59, 66, 318/67; 29/565, 566, 566.1, 566.2, 566.3, 566.4; 83/559, 560, 563, 651, 662; 144/285, 286 R; 248/51; 408/125, 135, 146, 199, 238, 239, 240, 714

[56] References Cited

U.S. PATENT DOCUMENTS

| | | |
|---|---|---|
| 1,463,168 | 7/1923 | Kintzing . |
| 2,299,887 | 10/1942 | Fell . |
| 2,422,117 | 6/1947 | Mercier . |
| 2,674,701 | 4/1954 | Maseritz . |
| 2,706,794 | 4/1955 | Rogers . |
| 2,707,754 | 5/1955 | Ludwig . |
| 2,944,120 | 7/1960 | Ruben . |
| 3,629,606 | 12/1971 | Mathey ............................ 318/293 X |
| 3,980,848 | 9/1976 | Schulz et al. . |
| 3,980,849 | 9/1976 | Straihammer . |
| 4,257,103 | 3/1981 | Suzuki et al. ................... 318/625 X |
| 4,497,353 | 2/1985 | Sproat, Jr. . |
| 4,586,398 | 5/1986 | Yindra . |
| 4,641,069 | 2/1987 | Fujioka et al. ..................... 318/625 |

Primary Examiner—Bentsu Ro

[57] ABSTRACT

A work station having a plurality of tools permits selection, operation and speed control of individually selected tools using a common speed control for each tool. Each of the tools includes a tool head such as a cutter, rasp, or other forming or finishing tool supported at the end of a flexible drive shaft rotatable by a motor. A free end portion of the drive shaft includes a holding portion to permit manipulation of the tool but by an operator. A set of berths is located at the work surface with each berth configured to receive respective end portions of the drive shafts. A switch is provided in each berth for electrically connecting each of the motors to the common speed control which is operable by a foot pedal for controlling the speed of a selected tool. Under this arrangement, an operator at the work station can manipulate any one of the work tools without the burden of manipulating the tool speed which is pedal controlled. Thus any selected number of tools are individually operable by a single speed control device.

11 Claims, 3 Drawing Sheets

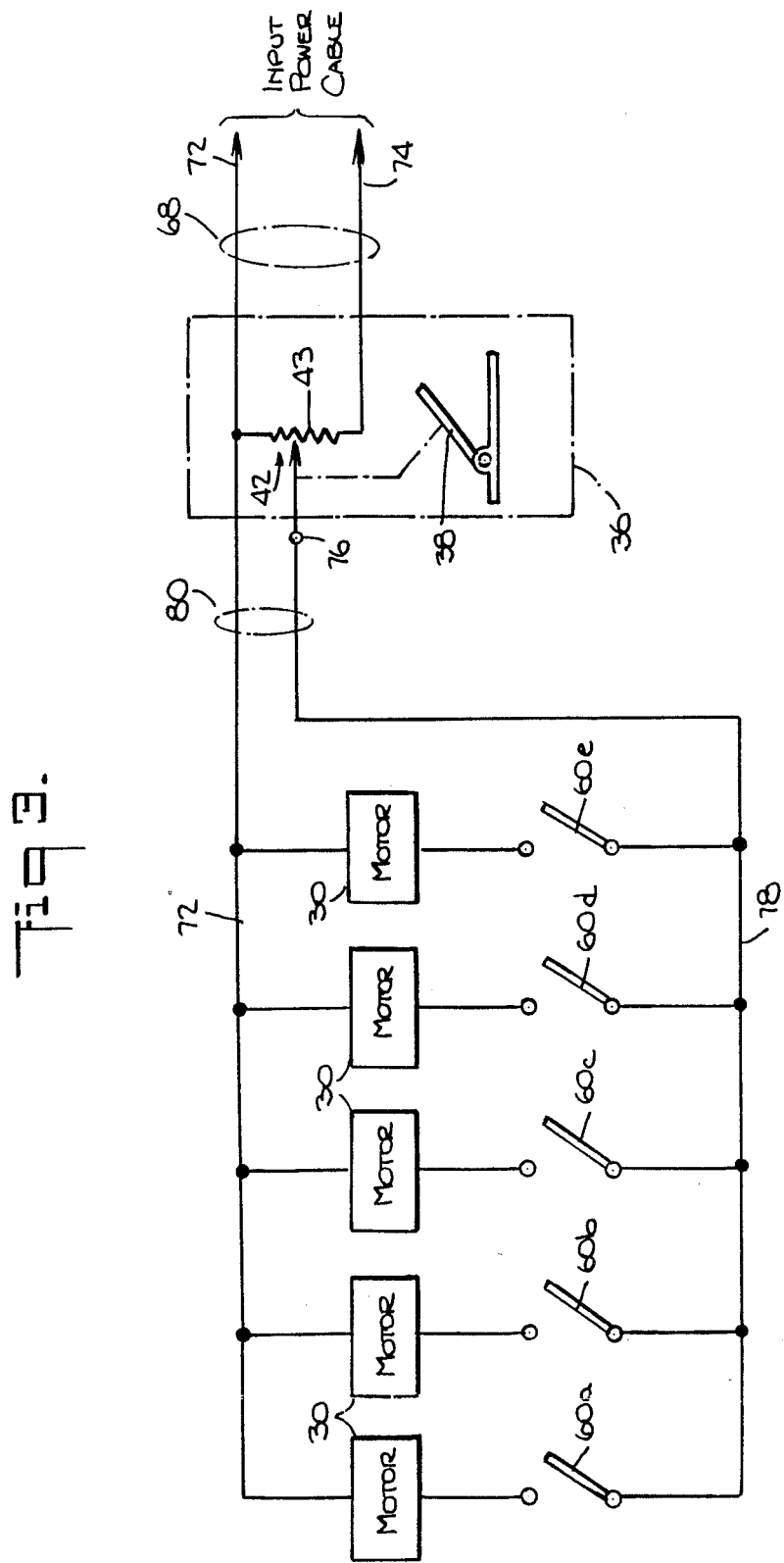

INTEGRATED TOOL CONTROL FOR WORK STATION

BACKGROUND OF THE INVENTION

This invention relates to control devices for power tools and, more particularly, to a common speed control selectively applicable to individual tools among a plurality of tools at a work station.

Of particular interest are work stations which use tools wherein the tool bit or tool head is mounted and driven at a location spaced from the primary drive member for the tool.

Numerous tools with rotatable tool heads, for example, are widely used at work stations in industrial craft operations involving the fashioning of jewelry and accessories and in dental offices or laboratories.

A well-known example of the use of such tools is the dental drill which is driven at one location and operated or manipulated by the dentist at another location. Such arrangement is desirable because of the need to manipulate the drill in many directions in a confined area as in the filling of dental cavities. It is noted that, in the case of the dental drill, the primary drive member may be an air turbine.

Another known power tool having a portable electric motor as the primary drive member includes an elongated flexible drive that holds a tool bit remotely from the motor housing in a holding device that permits easy manipulation of the tool bit. The elongated flexible drive separates the tool bit from the motor and facilitates intricate manual operation of the tool bit at desired locations in various different orientations.

One aspect of considerable interest in the use of such power tools is speed control of the tool bit. It is well known that certain types of cutting, grinding and polishing operations are best performed at relatively low rotational speeds, while other tooling operations are best performed at higher rotational speeds.

Various types of speed control devices for electric motors are known, whether the motor be connected directly to a tool bit as in a hand-held drill, or indirectly connected to the tool bit by generation of an air blast for driving a turbine as in the dental drill, or by a flexible rotatable shaft as in a Bowden cable drive for an electric motor. Indeed, such speed controls vary from a rheostat or variable resistor inserted in the power line of a motor to closedloop feedback control as is employed in servomechanisms.

The rheostat is widely employed in speed control devices because of its relatively simple construction, and the facility with which it can be incorporated into existing motor designs. For example, it is common practice to have a trigger-operated rheostat in hand-held electrically-powered tools. Alternatively, the rheostat can be operated by a foot pedal to facilitate manipulation of the tool as is common practice with dental drills.

In many industrial, professional or domestic work stations, in which several tools may be employed, a work project, such as the fashioning of an object from wood or metal often involves several different operations on a particular workpiece. For example, one drill with a large diameter bit and another drill with a small diameter bit may be needed. In addition, a rotatable rasp, a rotatable wire brush, and a rotatable sanding disk may be desired.

In a well-organized work station, several individual power tools, each with its own particular tool head or tool bit are positioned within easy reach of an operator to permit ready selection of one tool or another. However, in most presently known work stations having a plurality of tools, individual speed controls which can be hand or foot operated are provided for each tool.

Tools which require manual speed control by a trigger, for example, are usually more difficult to manipulate than tools having pedal controlled speed because during manual speed control, the weight of the motor is generally borne by the hand which manipulates the tool.

In the case of tools having speed controls operated by a foot pedal, each tool is normally provided with separate foot pedals. A plurality of foot pedals can cause confusion to a tool operator who may find it necessary to glance down below a workbench to ascertain that the proper foot pedal is being activated. A further disadvantage of individual foot pedal controls is that numerous pedal controls are required, even though the tools at a work station are ordinarily operated one at a time.

It is thus desirable to provide a single control for speed actuation of individual selected tools at a work station having a plurality of tools.

OBJECTS AND SUMMARY OF THE INVENTION

Among the several objects of the invention may be noted the provision of a novel speed control device for selective actuation of individual tools grouped together at a work station, a novel speed control device which functions as a common speed control for individually selected tools at a work station, a novel foot actuated speed control device which controls the speed of a selected one of a plurality of tools at a work station, and a novel speed control device for a plurality of tools at a work station.

Other objects and features of the invention will be in part apparent and in part pointed out hereinafter.

The tool control system, in accordance with the invention, provides for an integrated control of speed of a plurality of motorized tools at a work station. Speed control is accomplished by the use of a single pedal for operating a single rheostat which is electrically switchable to the motorized tool selected for operation. While the rheostat is contemplated as the speed control for the motors of all selected tools, other forms of speed control can be employed, provided each of the motors employs the same form of speed control.

In accordance with a feature of the invention, the tools are mounted on a rack wherein each tool is provided with an individual rack section, or berth, having a switch for connecting the single speed control to the tool. When a tool is in its berth, the switch at the berth is in the disconnect position wherein the speed control is disconnected from the tool.

An actuating lever of the tool is spring-biased, for example, and is located in the tool berth in a depressed position to disconnect the tool from the speed control upon insertion of the tool in its berth. Upon removal of a tool from its berth, the activating lever moves to a connect position to provide electrical connection of the speed control to the tool. Thus, all of the tools maintained in their respective berths are inoperable and the selected tool that is removed from its berth is operable by the speed control.

The invention accordingly comprises the constructions hereinafter described, the scope of the invention being indicated in the claims.

DESCRIPTION OF THE DRAWINGS

In the accompanying drawings.

Corresponding reference characters indicate corresponding parts throughout the several views of the drawings.

DETAILED DESCRIPTION OF THE INVENTION

Figure 1:
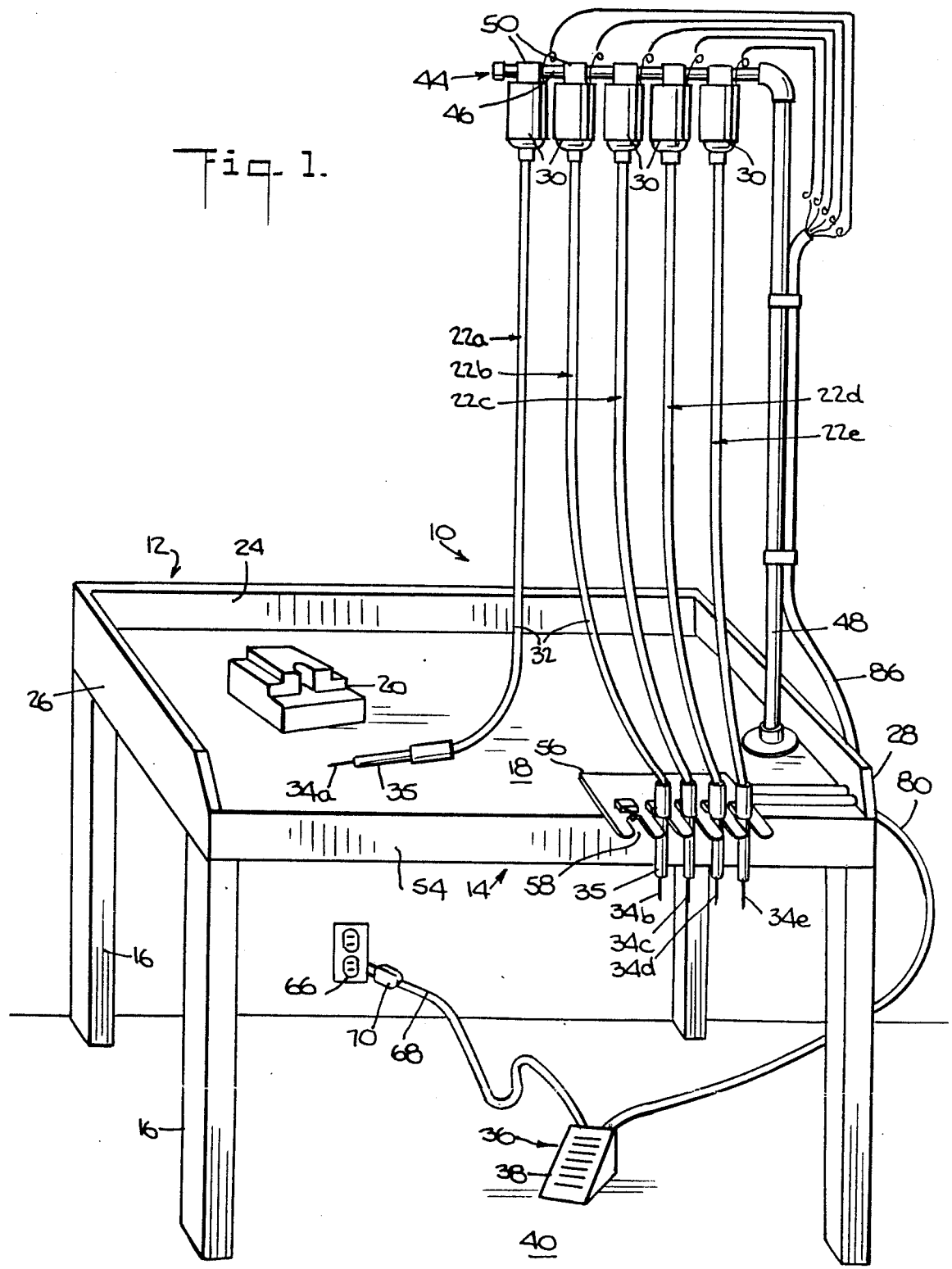
FIG. 1 is a simplified schematic view of a work station having a plurality of tools interconnected by an integrated motor control system incorporating one embodiment of the invention.

A work station incorporating one embodiment of the invention is generally indicated by the reference number 10 in FIG. 1.

The work station 10 comprises a work bench 12 formed of a table top 14 supported by legs 16. The table top 14 has a flat work surface 18 which supports a workpiece 20. The workpiece 20 can be hand-held, table-supported, or held in a vice (not shown) or other suitable holding device that can be attached to the table top 14. In general, the workpiece 20 is positionable on the work bench 12 at a suitable location for the performance of cutting and other shaping operations, employing any one of a set of tools such as 22a, 22b, 22c, 22d and 22e. Although five tools 22a-22e are shown, any number of tools may be employed at the work station 10. The table top 14 is also provided with side framing 24, 26 and 28, to partially enclose the work surface 18.

Each of the tools 22a-22e comprises a motor 30 and a flexible drive 32 which couples power outputted by the motor 30 to a respective tool head 34a, 34b, 34c, 34d and 34e. Each of the tool heads 34a-34e is held in a holding means 35 provided at the end of each of the flexible drives 32. The holding means 35, which is elongated to serve as a handle for manipulating the tool heads 34a, 34b, 34c, 34d and 34e also includes a collet (not shown) for securing the respective tool heads 34a-34e to the respective drives 32. The tool head 34a, for example, can be a rotary saw, the tool head 34b can be a grinder, the tool head 34c can be a polishing element, the tool head 34d can be a drill and the tool head 34e can be a rasp, all of which are used to form and finish the work piece 20.

Preferably, each of the motors 30 is an electric motor of identical construction. The motors 30 are operable at variable speeds selectable by a common speed control device, such as a speed controller 36. The speed controller 36 includes a depressible foot pedal 38 provided on a floor surface 40 beneath the bench 12 at a convenient location for foot operation at the work station 10.

Figure 2:
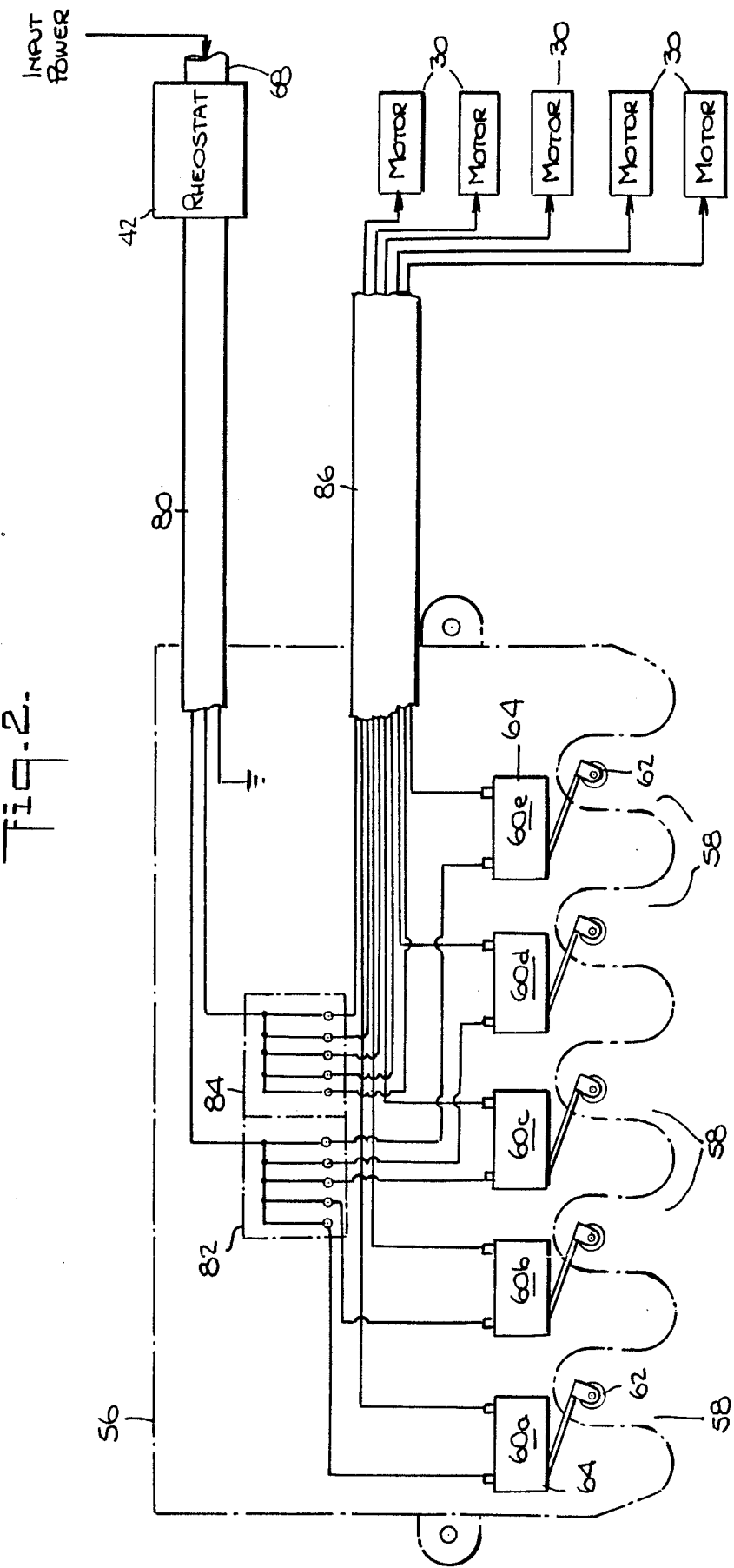
FIG. 2 is a simplified schematic diagram of an interconnection of switching apparatus at the work station of FIG. 1 with a plurality of motors and a common rheostat; and, FIG. 3 is an electrical schematic diagram of the switch interconnection shown in FIG. 2.

In a preferred embodiment of the invention, the controller 36 includes a rheostat 42 (FIGS. 2 and 3) for varying the amount of current and voltage applied to a selected motor 30. Movement of the rheostat 42 is controlled by the foot pedal 38 thus enabling an operator's hands to remain free of the speed-control function to more readily engage in the forming and finishing of the workpiece 20.

The tools 22 are supported by a frame 44 which includes a horizontal arm 46 and a vertical leg 48 mounted or secured to the bench 12 by a suitable mounting means 49. Each of the motors 30 are suspended, from the arm 46 by, for example, a ring 50 connected to the motor and disposed around the arm 46 in a suitable known manner to prevent sliding. The motors 30 and their corresponding flexible drives 32 are thus supported by the arm 46.

A holder plate 56 is disposed on the work surface 18 near a front portion 54 of the table top 14. As most clearly shown in FIG. 2, the holder plate 56 is formed with spaced recesses or berths 58 for receiving respective tool holding means 35 of the tools 22a-22e. Respective switches 60a, 60b, 60c, 60d and 60e are located in registration with corresponding berths 58. Each of the switches 60a-60e is provided with a movable member such as a lever 62 that pivots toward and away from respective outer cases 64 of the switches 60a-60e.

The levers 62 are normally biased to extend into the respective berths 58 of the tools 22a-22e to a position characterized as a switch-on position. In the absence of a respective tool holding means 35 in a respective berth 58, the corresponding lever 62 can project toward a central portion of the berth 58 in the switch on position. However, the presence of a respective holding means 35 in a respective berth 58, causes the corresponding lever 62 to pivot toward the switch case 64 to a position characterized as a switch-off position.

Thus, movement of any lever 62 toward the switch case 64 results in the opening of a corresponding switch 60a-60e to prevent the flow of electric current through the switches. Upon removal of a tool holding means 35 from its respective berth 58, the respective switch lever 62, being spring-loaded, moves into the berth 58 to close the selected switch 60a-60e and allow passage of electric current through the selected switch 60.

For example, referring to FIG. 1, the tools 22b-22e are nested in their respective berths 58 while the tool 22a is removed from its berth for operation on the workpiece 20. The corresponding array of switch positions for the tools 22a-22e is shown in FIG. 3 wherein the four switches 60b-60e corresponding to the berthed tools 22b-22e are open, and the switch 60a of the tool 22a is closed to provide electric current to the motor 30 of the tool 22a.

The motors 30 for each of the tools 22a-22e are provided with a known source of power, such as a wall-mounted outlet 66 into which an electric cable 68 is connected via a plug 70. The cable 68 includes two conductors 72 and 74 (FIG. 3) which are connected to opposed end terminals of a resistive element 43 of the rheostat 42. A center tap terminal 76 of the rheostat 42 slidably contacts the resistive element 43, and is mechanically connected to the foot pedal 38 for movement along the resistive element in accordance with the depressed position of the foot pedal 38.

The conductor 72 connects with one terminal of each of the motors 30. The center terminal 76 connects with one terminal of each of the switches 60a-60e. Connection between the center tap terminal 76 and the switches 60 is made by a conductor 78. Each of the motors 30 is serially connected by one of the switches 60a-60e between the conductor 72 and the terminal 76.

As shown in FIG. 3, closure of a respective switch 60a-60e allows current to flow via the corresponding motor 30 while the magnitude of the current is dependent on the position of the center terminal 76 of the rheostat 42. The coupling of electric power from the rheostat 42 to the series circuits of the motors 30 and the switches 60a–60e is provided by a cable 80, which cable comprises the conductors 72 and 78.

If desired, both the cables 80 and 68 may include an additional conductor (not shown) which serves as a ground for grounding the motors 30 to a ground connection (not shown) within the outlet 66. Connection of the conductors 72 and 78 to the terminals of the motors 30 and the switches 60a–60e is accomplished by use of terminal blocks 82 and 84 (FIG. 2) disposed on the holder plate 56. Coupling of electrical conductors to the motors 30 from the plate 56 is facilitated by use of a cable 86 which includes conductors extending from terminals of the motors 30.

The integrated speed control system of the present invention enables an operator at the work station 10 to individually select and operate one of a plurality of work tools. An advantage of the invention evident from the foregoing description is that any selected tool is operable by a common foot pedal speed control to permit facile manipulation of the selected tool with hands-free control of the tool speed. The common speed control employed for all of the tools is operable through switches with actuation levers that automatically respond to insertion or removal of a tool from its berth.

In view of the above, it will be seen that the several objects of the invention are achieved and other advantageous results attained.

As various changes can be made in the above constructions without departing from the scope of the invention, it is intended that all matter contained in the above description or shown in the accompanying drawings shall be interpreted as illustrative and not in a limiting sense.

What is claimed is:

1. An integrated control system for a work station comprising:
    a speed control means;
    a plurality of power means for driving respective tools at the work station;
    means at the work station for selectively switching individual ones of the power means to the speed control means, and wherein each of said power means is provided with an output flexible drive member; and
    said switching means includes selector means responsive to the presence of respective ones of said flexible drive members, said switching means being activated to apply power via said speed control means to the selected power means for which the flexible drive member is removed from the switching means.

2. A speed control system for a plurality of motors comprising:
    speed control means connectable between said motors and an external source of power for varying an amount of power applied to a selected one of said motors, the speed of the selected motor varying in accordance with the amount of power applied to the selected motor;
    means for selectively switching individual ones of the motors to the speed control means for energizing any one of said motors with power from said source and wherein each of said motors is provided with an output flexible drive member; and
    said switching means includes selector means responsive to the presence of respective ones of said flexible drive members, said switching means being activated to apply power from the source via said speed control means to the selected motor for which the flexible drive member is removed from the switching means.

3. A system according to claim 2 wherein
    each of said motors is an electric motor, said power source provides electric power, and said switching means comprises a plurality of switches connected to terminals of respective ones of said motors;
    said selector means comprises a set of levers connected to respective ones of said switches and extending into positions occupied by respective ones of said flexible drive members during periods of non-use of respective ones of said motors; and
    said speed control means comprises a variable resistive element to be connected serially between said source and said motors, said speed control means has a first terminal and a second terminal, each of said motors connects with said first terminal, and each of said switches connects with said second terminal.

4. An integrated control system for a work station comprising:
    supporting means;
    a speed control means;
    a plurality of power means for driving respective tools at the work station;
    means at the work station for selectively switching individual ones of the power means to the speed control means and wherein said switching means includes a plurality of switch actuation means for contacting individual ones of said power means and wherein said tools each have respective tool heads;
    each of said power means comprises an electric motor supported within a housing, and a flexible drive having end portions mechanically connecting the tool head of individual ones of said respective tools to the motor;
    said supporting means comprising a plurality of berths for receiving the respective end portions of said flexible drives; and
    each of said switch actuation means comprises a movable member extending from said switching means into respective ones of said berths.

5. A system according to claim 4 wherein said work station comprises a work surface for supporting a work piece to be operated on by said tool heads powered by said motors; and
    said berths are provided at said work surface for easy access by an operator at the work station.

6. A system according to claim 4 wherein said end portions include holding means for facilitating manipulation of respective ones of said tool heads extending from respective ones of said flexible drives.

7. A system according to claim 4 wherein said tool heads comprise a rotatable tool bit.

8. A system according to claim 4 wherein
    each of said electric motors is powered with electric current provided by power lines connecting to the respective motors;
    said speed control means is a pedal-operated rheostat connectable by said switching means to individual ones of said power lines of respective ones of said motors; and each of said movable members is normally biased into a first actuated position corresponding to electrical connection of respective ones of said motors to said rheostat, said movable members being normally positioned in a second deactuated position corresponding to electrical disconnection of respective ones of said motors to said rheostat when the respective end portions are positioned in their respective berths, such that removal of a selected end portion from its respective berth permits individual operation of its corresponding tool head while other said heads in their respective berths are inoperable.

9. A system according to claim 4 wherein said speed control means includes a depressible foot pedal arranged such that the speed of the selected motor varies in accordance with the amount of depression of said foot pedal.

10. A system according to claim 9 wherein the speed control means includes a rheostat for varying the amount of current and voltage applied to the selected motor, movement of the rheostat being controlled by the foot pedal.

11. A system according to claim 4 further comprising means for supporting said power means at said work station adjacent said switching means.

* * * * *